(12) United States Patent
Das et al.

(10) Patent No.: US 11,354,339 B2
(45) Date of Patent: Jun. 7, 2022

(54) METHOD AND SYSTEM FOR CLUSTERING USERS USING COGNITIVE STRESS REPORT FOR CLASSIFYING STRESS LEVELS

(71) Applicant: Tata Consultancy Services Limited, Mumbai (IN)

(72) Inventors: Deepan Das, Kolkata (IN); Shreyasi Datta, Kolkata (IN); Tanuka Bhattacharjee, Kolkata (IN); Anirban Dutta Choudhury, Kolkata (IN); Arpan Pal, Kolkata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 523 days.

(21) Appl. No.: 16/506,505

(22) Filed: Jul. 9, 2019

(65) Prior Publication Data
US 2020/0012665 A1 Jan. 9, 2020

(30) Foreign Application Priority Data
Jul. 9, 2018 (IN) .............................. 201821025608

(51) Int. Cl.
*G06F 16/00* (2019.01)
*G06F 16/28* (2019.01)
(Continued)

(52) U.S. Cl.
CPC ........... *G06F 16/285* (2019.01); *G16H 15/00* (2018.01); *A61B 5/16* (2013.01); *A61B 5/369* (2021.01); *A61B 5/4088* (2013.01)

(58) Field of Classification Search
CPC combination set(s) only.
See application file for complete search history.

(56) References Cited

U.S. PATENT DOCUMENTS

| | | | |
|---|---|---|---|
| 8,539,359 B2 | 9/2013 | Rapaport et al. | |
| 10,019,716 B1 * | 7/2018 | Ainslie | G06Q 30/016 |

(Continued)

OTHER PUBLICATIONS

Cho, Y. et al. (Dec. 2018). "Instant Automated Inference of Perceived Mental Stress through Smartphone PPG and Thermal Imaging," *Journal of Medical Internet Research/JMIR Mental Health—Special Issue on Computing and Mental Health*, 24 pages.

(Continued)

*Primary Examiner* — Farhan M Syed
(74) *Attorney, Agent, or Firm* — Finnegan, Henderson, Farabow, Garrett & Dunner LLP (57) ABSTRACT

A method and system for clustering users using cognitive stress report for classifying stress levels is provided. Detection and monitoring of cognitive stress experienced by users while performing a task is very crucial. The method includes receiving, user evaluated cognitive stress reports and the physiological signals of the user during the performance of the task. A normalized cognitive report is generated from the user evaluated cognitive stress report by computing mode and range value. The normalized cognitive stress reports of the users are used to cluster the users into a primary cluster and a secondary cluster. Feature sets are extracted from the physiological signals of the said users associated with the primary cluster. Using the said feature sets a classifier model is trained to classify the cognitive stress levels of the users as stressful class or stressless class.

20 Claims, 8 Drawing Sheets

(51) Int. Cl.
*G16H 15/00* (2018.01)
*A61B 5/16* (2006.01)
*A61B 5/00* (2006.01)
*A61B 5/369* (2021.01)

(56) References Cited

U.S. PATENT DOCUMENTS

| | | | |
|---|---|---|---|
| 10,417,653 B2* | 9/2019 | Milton | H04W 4/029 |
| 11,188,935 B2* | 11/2021 | Milton | G06Q 30/02 |
| 2015/0186617 A1* | 7/2015 | Cardonha | G16H 15/00 |
| | | | 706/52 |
| 2017/0344706 A1* | 11/2017 | Torres | A61B 5/7264 |

OTHER PUBLICATIONS

Matthews, G. et al. (2013). "Profiling Task Stress with the Dundee Stress State Questionnaire," Chapter 2 In *Psychology of Stress.* Leandro Cavalcanti and Sofia Azevedo ed., Nova Science Publishers, Inc.; pp. 49-91.

* cited by examiner

FIG.6 a) Raw EEG from FP1 electrode, showing ocular artifacts b) Processed EEG from FP1 electrode, with artifacts removed (c) Raw GSR (d) Processed GSR (e) Raw PPG (f) Processed PPG

FIG.9

METHOD AND SYSTEM FOR CLUSTERING USERS USING COGNITIVE STRESS REPORT FOR CLASSIFYING STRESS LEVELS

PRIORITY CLAIM

This U.S. patent application claims priority under 35 U.S.C. § 119 to India Application No. 201821025608, filed on Jul. 9, 2018. The entire contents of the aforementioned application are incorporated herein by reference.

TECHNICAL FIELD

The disclosure herein generally relates to classification of cognitive stress levels, and, more particularly, to a method and system for clustering users using cognitive stress report for classifying stress levels.

BACKGROUND

Stress is a complex phenomenon that impacts human body and mind responding to stressful stimulus at various levels. Early detection of stress can assist in maintaining the mental wellbeing of a large section of the vulnerable population. According to World Health Organization, depression and anxiety related disorders can be attributed to prolonged exposure to stressful conditions. Monitoring stress continuously may help the users better understand their stress patterns. These patterns provide physicians more reliable data for timely interventions and prevention of chronic mental disorders. Hence, a methodology for automated detection and analysis of stress is necessitated for providing valuable information about the predictive performance of certain features in stressful contexts.

Conventionally, various techniques have been proposed to detect and monitor cognitive stress of users using physiological signals and/or user evaluated cognitive stress reports. These techniques use features derived from physiological signals and/or user evaluated cognitive stress report for analyzing the level of cognitive stress experienced during the performance of the task. However, these techniques limit in clustering the users having similar distribution of stress experienced while performing the task and these clustered user data are further utilized to train a classifier model for classifying cognitive stress levels thereby improving the performance of the trained classifier model.

In an existing system, analysis, monitoring and classification of the level of stress using physiological signals and/or the self-report provided by the user is a viable choice. However, this system limits in analyzing user evaluated cognitive stress report of each user to cluster users based on the cognitive stress experienced during the performance of the task that improves classification of cognitive stress from the physiological signals of the user.

SUMMARY

Embodiments of the present disclosure present technological improvements as solutions to one or more of the above-mentioned technical problems recognized by the inventors in conventional systems. For example, in one embodiment, a method and system for clustering users using cognitive stress report for classifying stress levels. The method includes receiving, a plurality of cognitive stress reports recorded for a plurality of users while performing a task comprising a plurality of levels, wherein each cognitive stress report among the plurality of cognitive stress reports corresponds to a user among the plurality of users, and each cognitive stress report records user-evaluated estimate of the cognitive stress experienced by each user at each level among the plurality of levels repeated for a plurality of trials performed for the task by the user and a plurality of physiological signals for each user from a plurality of sensors. Here, each cognitive stress report comprises a plurality of cognitive stress parameters recorded for the plurality of levels during the performance of the task. Further, the method generates, a plurality of normalized cognitive stress report for each user, wherein the normalized cognitive stress comprises an estimate of the cognitive stress experienced by the user at each level of the task for the plurality of trials. Further, the plurality of users are clustered based on the plurality of normalized cognitive stress reports using an unsupervised clustering mechanism to generate a primary cluster and a secondary cluster such that users of each cluster have similar distribution of normalized cognitive stress report for the plurality of trials of the task and users of different clusters have dissimilar distribution of normalized cognitive stress reports for the plurality of trials of the task. Furthermore, a plurality of feature sets are extracted from the plurality of physiological signals, the plurality of feature sets correlating with the cognitive stress experienced by the plurality of users associated with the primary cluster. Furthermore, using a feature ranking method, a subset is selected from the plurality of feature sets, for the plurality of users associated with the primary cluster. The selected features sets of the plurality of users associated with the primary cluster are segregated into a train user dataset and a test user dataset, wherein, the test user is randomly selected from the primary cluster and the remaining users associated with the primary cluster are used as train users. Furthermore, using the selected feature set of the train user dataset, a classifier model is trained for classifying stressful and stressless trials for the users of primary cluster. The trained classifier model is utilized to classify the plurality of trials of the test user dataset as stressful and stressless class.

In another aspect, a method and system for clustering users using cognitive stress report for classifying stress levels is provided. The system includes a processor, an Input/output (I/O) interface and a memory coupled to the processor is capable of executing programmed instructions stored in the processor in the memory to receive, a plurality of cognitive stress reports recorded for a plurality of users while performing a task comprising a plurality of levels, wherein each cognitive stress report among the plurality of cognitive stress reports corresponds to a user among the plurality of users, and each cognitive stress report records user-evaluated estimate of the cognitive stress experienced by each user at each level among the plurality of levels repeated for a plurality of trials performed for the task by the user and a plurality of physiological signals for each user from a plurality of sensors. Here, each cognitive stress report comprises a plurality of cognitive stress parameters recorded for the plurality of levels during the performance of the task. Further, the processors are configured by the instructions to generate, a plurality of normalized cognitive stress report for each user, wherein the normalized cognitive stress comprises an estimate of the cognitive stress experienced by the user at each level of the task for the plurality of trials. Further, the plurality of users are clustered based on the plurality of normalized cognitive stress reports using an unsupervised clustering mechanism to generate a primary cluster and a secondary cluster such that users of each cluster have similar distribution of normalized cognitive stress reports for the plurality of trials of the task and users of different clusters have dissimilar distribution of normalized cognitive stress reports for the plurality of trials of the task. Furthermore, the processors are configured by the instructions to extract a plurality of feature sets from the plurality of physiological signals, the plurality of feature sets correlating with the cognitive stress experienced by the plurality of users associated with the primary cluster. Furthermore, using a feature ranking method, a subset is selected from the plurality of feature sets, for the plurality of users associated with the primary cluster. The selected features sets of the plurality of users associated with the primary cluster are segregated into a train user dataset and a test user dataset, wherein, the test user is randomly selected from the primary cluster and the remaining users associated with the primary cluster are used as train users. Furthermore, using the selected feature set of the train user dataset, a classifier model is trained for classifying stressful and stressless trials for the users of primary cluster. The trained classifier model is utilized to classify the plurality of trials of the test user dataset as stressful and stressless class.

In yet another aspect, a non-transitory computer readable medium having embodied thereon a computer program for executing a method for receiving, a plurality of cognitive stress reports recorded for a plurality of users while performing a task comprising a plurality of levels, wherein each cognitive stress report among the plurality of cognitive stress reports corresponds to a user among the plurality of users, and each cognitive stress report records user-evaluated estimate of the cognitive stress experienced by each user at each level among the plurality of levels repeated for a plurality of trials performed for the task by the user and a plurality of physiological signals for each user from a plurality of sensors. Here, each cognitive stress report comprises a plurality of cognitive stress parameters recorded for the plurality of levels during the performance of the task. Further, the method generates, a plurality of normalized cognitive stress report for each user, wherein the normalized cognitive stress comprises an estimate of the cognitive stress experienced by the user at each level of the task for the plurality of trials. Further, the plurality of users are clustered based on the plurality of normalized cognitive stress reports using an unsupervised clustering mechanism to generate a primary cluster and a secondary cluster such that users of each cluster have similar distribution of normalized cognitive stress reports for the plurality of trials of the task and users of different clusters have dissimilar distribution of normalized cognitive stress reports of the plurality of trials of the task. Furthermore, a plurality of feature sets are extracted from the plurality of physiological signals, the plurality of feature sets correlating with the cognitive stress experienced by the plurality of users associated with the primary cluster. Furthermore, using a feature ranking method, a subset is selected from the plurality of feature sets, for the plurality of users associated with the primary cluster. The selected features sets of the plurality of users associated with the primary cluster are segregated into a train user dataset and a test user dataset, wherein, the test user is randomly selected from the primary cluster and the remaining users associated with the primary cluster are used as train users. Furthermore, using the selected feature set of the train user dataset, a classifier model is trained for classifying stressful and stressless trials for the users of primary cluster. The trained classifier model is utilized to classify the plurality of trials of the test user dataset as stressful and stressless class.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION OF EMBODIMENTS

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

The embodiments herein discloses a method and system for clustering users using cognitive stress report for classifying stress levels. The proposed method and system, provides clustering a plurality of users for classifying their cognitive stress levels using a low cost simple solution. The system 102, may alternatively be referred as cognitive stress classification system. In one embodiment the system utilizes the plurality of user evaluated cognitive stress reports and a plurality of physiological signals corresponding to each user among the plurality of users at each level among a plurality of levels for a plurality of trials. Each cognitive stress report of the user among the plurality of users comprises an estimate of cognitive stress for a plurality of cognitive stress parameters experienced by each user while performing a task. The task includes various levels, wherein each level variates based on the induced stress or difficulties to be experienced by each user during the performance of the task. Here, the plurality of physiological signals are captured from a plurality of physiological sensors, wherein the plurality of physiological signals comprises Electroencephalogram (EEG) signal to estimate the neural responses of the user, Photoplethysmogram (PPG) signal to analyze cardiac parameters of the user, and Galvanic Skin Response (GSR) to determine changes due to variations in skin conductance of the user. The present disclosure is further capable of clustering users among the plurality of users based on a plurality of normalized cognitive stress reports generated from the plurality of user evaluated cognitive stress reports. Each normalized cognitive stress report among the plurality of normalized cognitive stress reports is an estimate of cognitive stress obtained from a plurality of cognitive stress parameters experienced by each user during the performance of the task at each level for the plurality of trails. Further, users are clustered as a primary cluster and a secondary cluster to classify each level from the trials as stressful class and stressless class using a trained classifier model. This classifier model is trained using features derived from the physiological signals of users belonging to the same cluster.

Referring now to the drawings, and more particularly to FIG. 1 through FIG. 9, where similar reference characters denote corresponding features consistently throughout the figures, there are shown preferred embodiments and these embodiments are described in the context of the following exemplary system and/or method.

Figure 1:
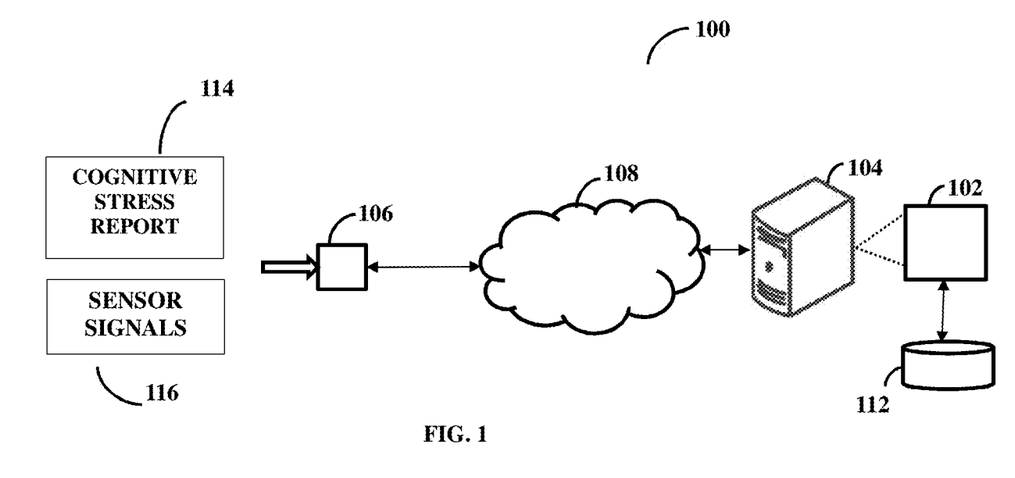
FIG. 1 illustrates a network implementation of a system for classifying cognitive stress levels from physiological signals using a user evaluated cognitive stress report, in accordance with an embodiment of the present disclosure.
Figure 2:
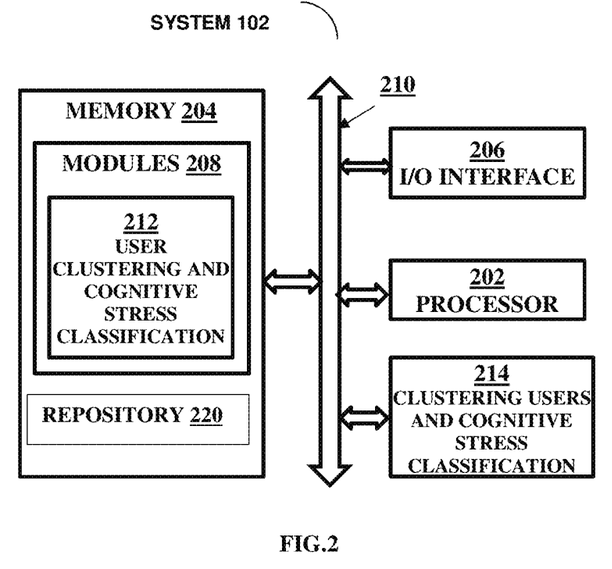
FIG. 2 illustrates a block diagram of the system for classifying cognitive stress levels of users, in accordance with an embodiment of the present disclosure.

FIG. 1 illustrates a network 100 implementation of a system 102 for classifying cognitive stress levels from physiological signals using a user evaluated cognitive stress report, in accordance with an embodiment of the present disclosure. The system 100 depicts data source 106, that receives the plurality of user evaluated cognitive stress reports recorded for the plurality of trials during the performance of the task and simultaneously captures the signal information from the plurality of physiological signals using the plurality of sensors 116 that includes Electroencephalogram (EEG) signal, Photoplethysmogram (PPG) signal and Galvanic Skin Response (GSR) for a plurality of users during the performance of the task. The cognitive stress classification system 102 may be externally coupled (as shown in FIG. 1) to the computing device 104 or may be internal (not shown) to the computing device 104. The plurality of user evaluated cognitive stress reports 114 and the plurality of physiological signals 116 of each user from the plurality of users are acquired through the data acquisition unit 106 and can be stored in the repository 220. The repository 220 may be external to the cognitive stress classification system 102 or internal to the cognitive stress classification system 102 (as shown in FIG. 2). In an embodiment, the data acquisition unit 106 may be directly connected to the cognitive stress classification system 102. In an embodiment, a plurality of data acquisition units 106 may be connected to the cognitive stress classification system 102 for clustering users based on their cognitive behavioral patterns at various levels of the task/tasks for each trial during the performance of the task. It will be understood that the system 102 may be accessed by multiple users through one or more user devices 104-1, 104-2 . . . 104-N, collectively referred to as user devices 104 hereinafter, or applications residing on the user devices 104. Examples of the user devices 104 may include, but are not limited to, a portable computer, a personal digital assistant, a handheld device, a Smartphone, a Tablet Computer, a workstation and the like. The user devices 104 are communicatively coupled to the system 102 through a network 106.

In an embodiment, the system 102 receives data from the data acquisition unit 106 through a network 108. The computing device 104, may be a wireless or a wired network, or a combination thereof. In an example, the network 108 can be implemented as a computer network, as one of the different types of networks, such as virtual private network (VPN), intranet, local area network (LAN), wide area network (WAN), the internet, and such. The network 108 may either be a dedicated network or a shared network, which represents an association of the different types of networks that use a variety of protocols, for example, Hypertext Transfer Protocol (HTTP), Transmission Control Protocol/Internet Protocol (TCP/IP), and Wireless Application Protocol (WAP), to communicate with each other. Further, the network 108 may include a variety of network devices, including routers, bridges, servers, computing devices, storage devices. The network devices within the network 108 may interact with the cognitive stress classification system 102 through communication links. In an embodiment, the computing device 104, which implements the cognitive stress classification system 102 can be a workstation, a mainframe computer, a general purpose server, a network server or the like. The components and functionalities of the system 102 are described further in detail with reference to FIG. 2.

FIG. 2 illustrates a block diagram of a system 102 for classifying cognitive stress levels of users, in accordance with an embodiment of the present disclosure. The cognitive stress classification system 102 includes or is otherwise in communication with one or more hardware processors such as a processor(s) 202, at least one memory such as a memory 204, and an I/O interface 206. The processor 202 (hardware processor), the memory 204, and the I/O interface(s) 206 may be coupled by a system bus such as a system bus 210 or a similar mechanism. The memory 204 further may include modules 208. In an embodiment, the modules 208 includes a user clustering and cognitive stress classification module 212 and other modules (not shown) for implementing functions of the cognitive stress classification system 102. In an embodiment, the modules 208 can be an Integrated Circuit (IC), external to the memory 204 (not shown), implemented using a Field-Programmable Gate Array (FPGA) or an Application-Specific Integrated Circuit (ASIC). The names of the modules of functional block within the modules 208 referred herein, are used for explanation and are not a limitation. Further, the memory 204 can also include the repository 220 (internal to the cognitive stress clustering and classification system 102 as shown in FIG. 2).

The I/O interface 206 may include a variety of software and hardware interfaces, for example, a web interface, a graphical user interface, and the like. The I/O interface 206 may include a variety of software and hardware interfaces, for example, interfaces for peripheral device(s), such as a keyboard, a mouse, an external memory, a camera device, and a printer. Further, the I/O interface 206 may enable the system 102 to communicate with other devices, such as web servers and external databases. The I/O interface 206 can facilitate multiple communications within a wide variety of networks and protocol types, including wired networks, for example, local area network (LAN), cable, etc., and wireless networks, such as Wireless LAN (WLAN), cellular, or satellite. For the purpose, the I/O interface 206 may include one or more ports for connecting a number of computing systems with one another or to another server computer. The I/O interface 206 may include one or more ports for connecting a number of devices to one another or to another server.

The hardware processor 202 may be implemented as one or more microprocessors, microcomputers, microcontrollers, digital signal processors, central processing units, state machines, logic circuitries, and/or any devices that manipulate signals based on operational instructions. Among other capabilities, the hardware processor 202 is configured to fetch and execute computer-readable instructions stored in the memory 204.

The memory 204 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, the memory 204 includes a plurality of modules 208 that includes routines, programs, objects, components, data structures, and so on, which perform particular tasks or implement particular abstract data types. The user clustering and cognitive stress classification module 212 of the system 102 can be configured to receive data from the data acquisition unit 106. The repository 220 may include a sensor data employed for physiological sensing of a user and the plurality of user evaluated cognitive stress reports.

In an embodiment, the system 102 obtains, the plurality of user evaluated cognitive stress reports recorded for each level among the plurality of levels repeated for the plurality of trials during the performance of the task. The level herein referred as stress induced based on difficulties while performing the task. The plurality of user evaluated cognitive stress reports comprises an estimate of cognitive stress assessed by each user for the plurality of cognitive stress parameters at each level for the plurality of trials while performing the task. Here, the plurality of cognitive stress parameters comprises a valence (V) parameter, an arousal (A) parameter and a dominance (D) parameter. Concurrently, the system 102 also receives the plurality of physiological signals captured using the plurality of physiological sensors for each user among the plurality of users during the performance of the task. Herein, the plurality of physiological signals includes, but are not limited to, information gathered from Electroencephalogram (EEG) signal to estimate the neural responses of the user, Photoplethysmogram (PPG) signal to analyze the variations in heart rate and other cardiac parameters of the user and Galvanic skin response (GSR) signal changes of the user, due to variations in skin conductance.

The system 102 further computes a mode value and a range value for the plurality of cognitive stress parameters associated with the plurality of user evaluated cognitive stress reports for each user among the plurality of users. Here, the mode value and the range value for the plurality of cognitive stress report of the plurality of users are utilized to generate the plurality of normalized cognitive stress reports. The normalized cognitive stress report includes an estimate of the cognitive stress experienced by each user at each level of the task during the plurality of trials. Further, the plurality of users are clustered into a primary cluster and a secondary cluster based on the plurality of normalized cognitive stress reports using an unsupervised learning technique such that users of each cluster have similar distribution of normalized cognitive stress reports for the plurality of trials of the task and users of different clusters have dissimilar distribution of normalized cognitive stress reports for the plurality of trials of the task. Further, the system 102 extracts a plurality of feature sets from the physiological signals of the users associated with the primary cluster. A subset of the features is selected from the plurality of feature sets for the plurality of users associated with the primary cluster using a feature selection technique like Maximum Relevance Minimum Redundancy (mRMR). The selected feature sets of the plurality of users associated with the primary cluster are segregated into a train user dataset and a test user dataset. Further, a classifier model is trained using the selected feature set for the train users for classifying the cognitive stress levels of test users of primary cluster. The trained classifier model is further utilized by the test user to determine the trials belonging to stressful class and stressless class. The components or modules and functionalities of the cognitive stress classification system 102 are described further in detail in conjunction with FIG. 3.

Figure 3:
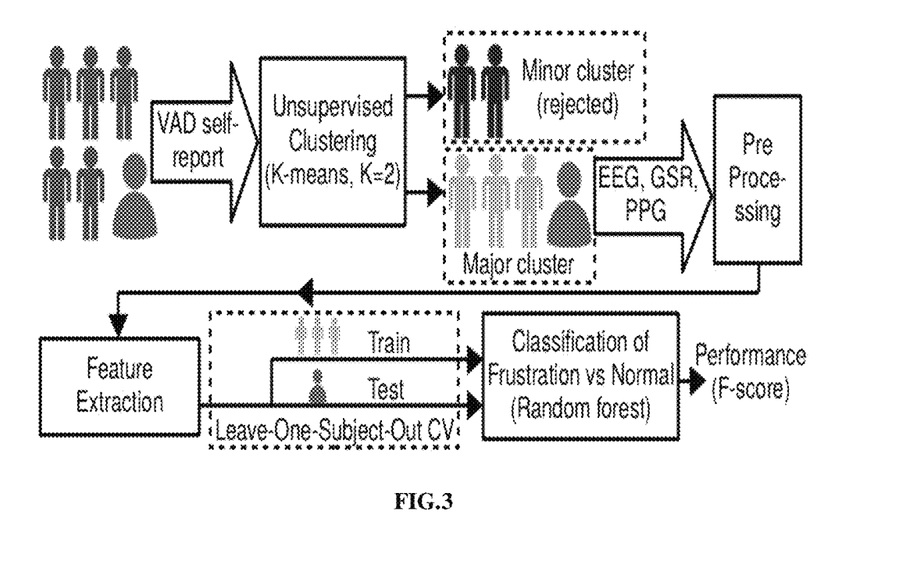
FIG. 3 illustrates an example functional architecture of the system for classifying cognitive stress levels of users from physiological signals by clustering the users using user evaluated cognitive stress report, in accordance with an embodiment of the present disclosure.

FIG. 3 illustrates an example functional architecture of the system 102 for classifying cognitive stress levels of users from physiological signals by clustering the users using user evaluated cognitive stress report, in accordance with an embodiment of the present disclosure. In one embodiment, the system 102 includes an unsupervised learning component, a preprocessing component, a feature extraction component and a classifier component. The unsupervised learning component is utilized to receive the plurality of users' self evaluated cognitive stress reports to segregate users into the primary cluster and the secondary cluster. The unsupervised learning component utilized a plurality of clustering techniques but not limited to k means clustering technique for clustering the plurality of users. The clustering component comprises the primary cluster and the secondary cluster. The users belonging to each cluster are so determined that users of same cluster have similar distribution of normalized cognitive stress report for the plurality of trials of the task and users of different cluster have dissimilar distribution of normalized cognitive stress report for the plurality of trials of the task. Further, the system 102 extracts a plurality of feature sets from the physiological signals for the users associated with the primary cluster. The preprocessing component obtains the plurality of physiological signals of the users associated with the primary cluster to remove the noise and artifacts present in the signals. The physiological signals obtained from the physiological sensors may be corrupted due to noise and artifacts. In order to de noise the physiological signals, the system 102 preprocesses the plurality of physiological signals to reduce noise.

The feature extraction component extracts the plurality of feature sets. The classifier component trains the classifier model using the selected feature sets for classifying the cognitive stress of the plurality of users of the primary cluster to determine stressful class and stressless class. The classifier component utilizes a random forest classifier model for classifying the users based on the cognitive stress experienced during the performance of the task.

Figure 4A:
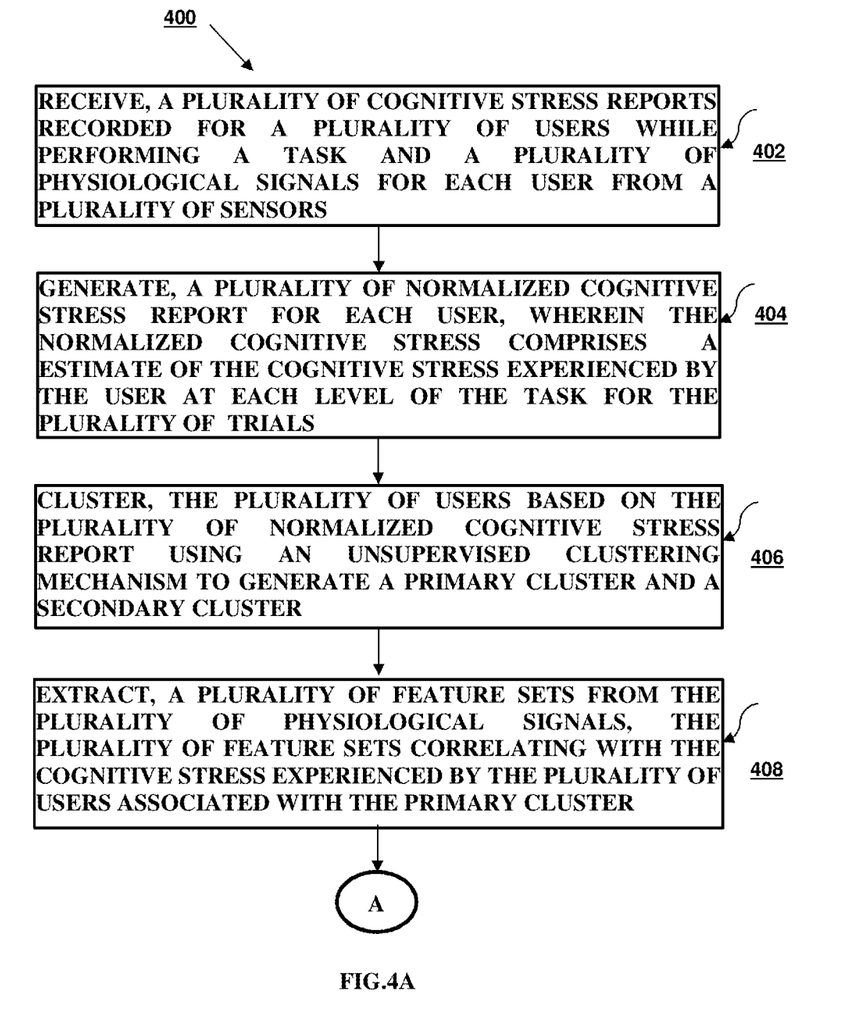
FIGS. 4A and 4B illustrate an example flow diagram of a method for classifying cognitive stress levels of users from physiological signals by clustering the users using self evaluated cognitive stress reports, in accordance with an embodiment of the present disclosure.
Figure 4B:
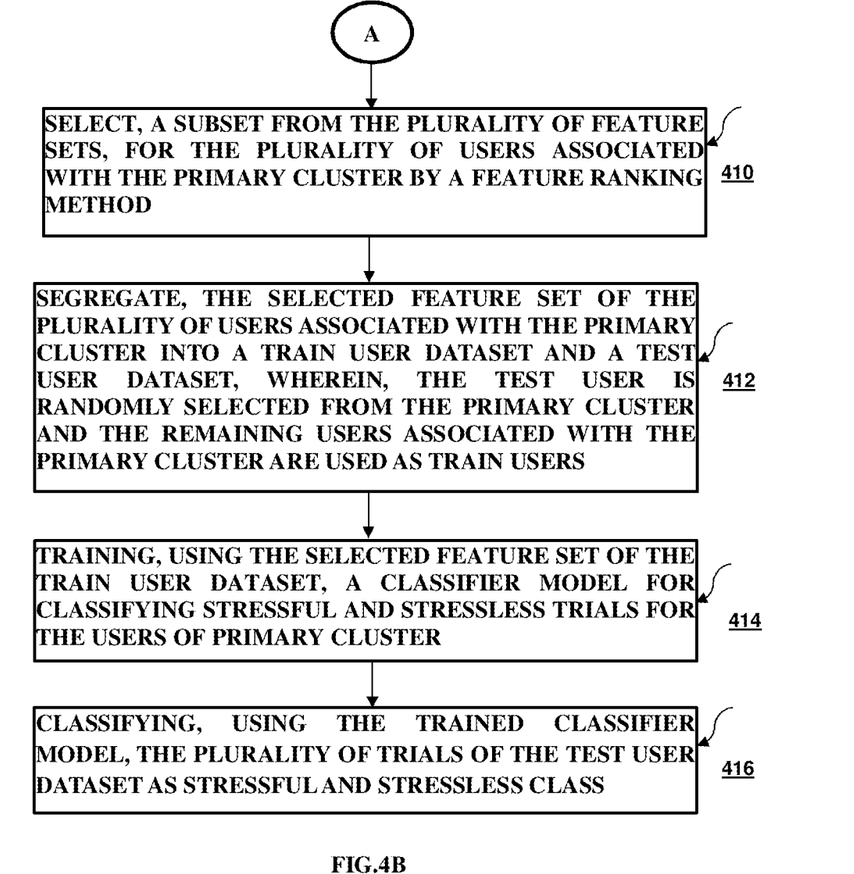
Figure 6:
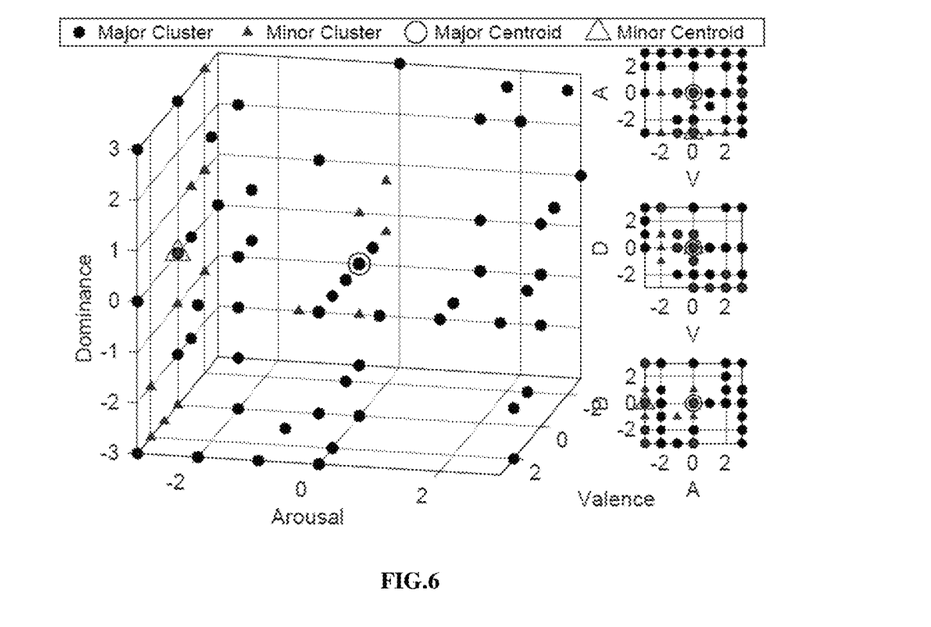
FIG. 6 illustrates clustering of users based on a plurality of normalized cognitive stress reports in conjunction with FIG. 3, in accordance with an embodiment of the present disclosure.

FIGS. 4A and 4B illustrate an example flow diagram of a method for classifying cognitive stress levels of users from physiological signals by clustering the users using self evaluated cognitive stress reports, in accordance with an embodiment of the present disclosure and FIG. 6 illustrates clustering of users based on a plurality of normalized cognitive stress report in conjunction with FIG. 3, in accordance with an embodiment of the present disclosure. The method 400 may be described in the general context of computer executable instructions. Generally, computer executable instructions can include routines, programs, objects, components, data structures, procedures, modules, functions, etc., that perform particular functions or implement particular abstract data types. The method 400 may also be practiced in a distributed computing environment where functions are performed by remote processing devices that are linked through a communication network. The order in which the method 400 is described is not intended to be construed as a limitation, and any number of the described method blocks can be combined in any order to implement the method 400, or an alternative method. Furthermore, the method 400 can be implemented in any suitable hardware, software, firmware, or combination thereof. In an embodiment, the method 400 depicted in the flow chart may be executed by a system 102, for example, the system 102 of FIG. 2. In an example embodiment, the system 102 may be embodied in an exemplary computer system.

At step 402 of the method 400, the one or more hardware processors 202 in conjunction with the user clustering and cognitive stress classification module 102 are configured to receive, the plurality of cognitive stress reports recorded for the plurality of users while performing a task and the plurality of physiological signals for each user from the plurality of sensors.

At step 404 of the method 400, the one or more hardware processors 202 in conjunction with the user clustering and cognitive stress classification module 102 are configured to generate, the plurality of normalized cognitive stress report for each user, wherein the normalized cognitive stress comprises an estimate of the cognitive stress experienced by the user at each level of the task for the plurality of trials. The plurality of normalized cognitive stress reports are generated using the mode and range value as mentioned.

Let $X_j^e$ be the set of the user evaluated estimates for the given levels j (j=1, 2, 10) for all trials, in either of valence, arousal or dominance (e=V, A or D). Let $M_j^e$=mode $(X_j^e)$, $D_j^e$=(range $(X_j^e)$)/5. For a user evaluated cognitive stress report $x_{j,k}^e$, given for trial k and emotion axis e, the rating is modified as $y_{j,k}^e=(x_{j,k}^e-M_j^e)/D_j^e$, (k=1, 2 . . . 15), $y_{j,k}^e$ being modified by the mode and range of user evaluated cognitive stress reports. Mode (measure of central tendency) of a subject's ratings in a single dimension reflects the subject's Tendency. Range (a more interpretable measure of deviation than standard deviation, in case of limited trials) reflects Excitability and Exaggeration.

At step 406 of the method 400, the one or more hardware processors 202 in conjunction with the user clustering and cognitive stress classification module 102 are configured to cluster, the plurality of users based on the plurality of normalized cognitive stress report using an unsupervised clustering mechanism to generate a primary cluster and a secondary cluster. K-means (K=2) clustering is performed on those plurality of normalized cognitive stress report vectors of each level. The primary cluster produced by the proposed scheme E comprises 8 levels totaling 117 instances and centroid at (0, 0, and 0) (levels characterized by moderate valence, arousal and dominance). The secondary cluster has centroid at (0, −3, and 0) (set apart by virtue of high arousal). This cluster, comprising 2 levels and 29 instances, is eliminated.

Figure 7:
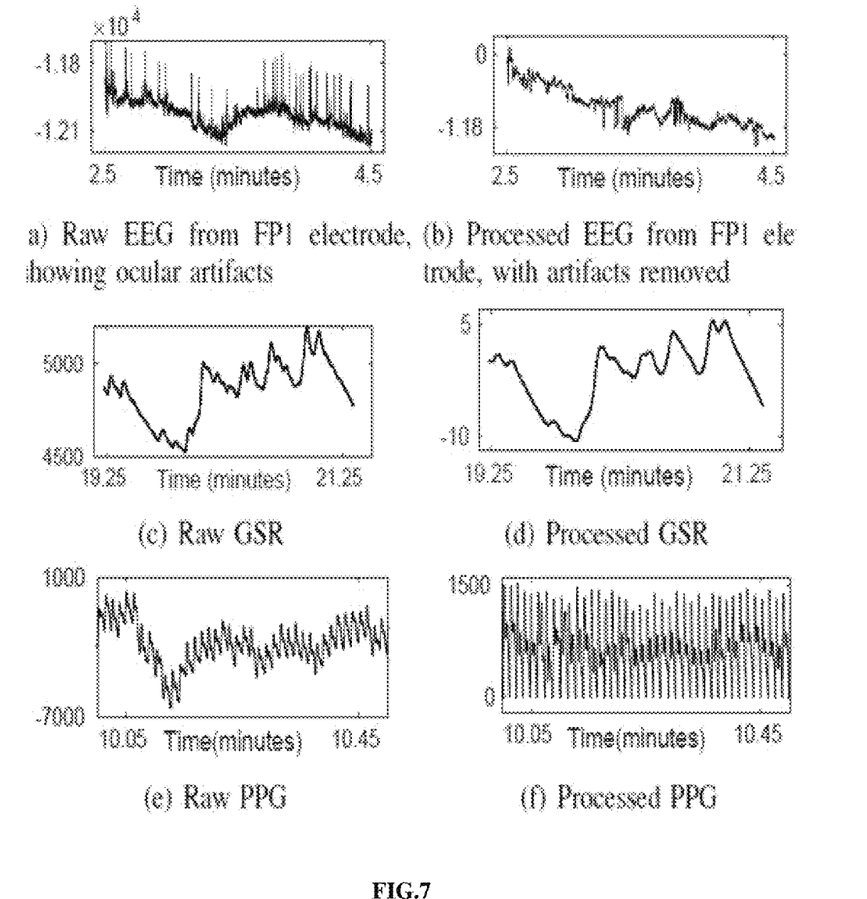
FIG. 7 illustrates observed raw and processed samples of physiological signals corresponding to Electroencephalogram (EEG), Galvanic Skin Response (GSR) and Photoplethysmogram (PPG) signals utilized in classifying cognitive stress levels of users, in accordance with an embodiment of the present disclosure.

At step 408 of the method 400, the one or more hardware processors 202 in conjunction with the user clustering and cognitive stress classification module 102 are configured to extract, a plurality of feature sets from the plurality of physiological signals, the plurality of feature sets correlating with the cognitive stress experienced by the plurality of users associated with the primary cluster. Considering an example with 2 consecutive gameplay (trials) blocks i−1 and i providing signals $S_{g,i-1}$ and $S_{g,i}$. Let the signal, recorded while the participant gave feedback for block i−1, be Sf, i−1. Here, choosing $S_{f,i-1}$ as baseline for $S_{g,i}$. S refers to all the signal modalities that includes EEG, EOG, EMG, GSR and PPG. All filters mentioned execute backward and forward filtering. All signals are available at 128 Hz sampling frequency. Considering, EEG physiological signal analysis, wherein no information is available about whether the power line interference is at 50 Hz or 60 Hz. Additionally, the power in the gamma band is concentrated around 45 Hz. Thus the signal at each of the 32 channels is passed through a $6^{th}$ order elliptical low pass filter having a cut-off frequency of 45 Hz. $EEG_{g,i}$ is normalized by subtracting the median of $EEG_{f,i-1}$, then dividing by the interquartile range. EOG and EMG, processed using the same technique, are used to do a regression-based artifact removal from EEG. According to the authors, this method can remove up to 80% of artifacts if the baseline consists of distinct eye-blinks and movements. But such a baseline was not incorporated into the experiment design of the AffPac dataset, thus making the artifact removal less effective. Spectrogram, with 2 s windows and 90% overlap, is computed using short-time Fourier transform. Window length is chosen to achieve the desired frequency resolution, while the number of samples per window and overlap were both recommended. Next, features are extracted separately from each channel of $EEG_{g,i}$ and re-referenced by considering $EEG_{f,i-1}$ as the rest state EEG. Final EEG feature set consists of 32*3+(32+14)*6*5=1476 features. The galvanic skin response (GSR) signal is down sampled to 64 Hz and then low pass filtered at 5 Hz using a 32nd order FIR constrained equiripple filter. Next, the signal is normalized by subtracting the minimum of $GSR_{f,i-1}$ and dividing by the range of the same. Finally, the best fit linear trend is removed from the signal. Samples of raw and processed GSR are illustrated in FIG. 7 as described. 18 features are extracted from GSR. The methods for Photoplethysmogram (PPG) signal preprocessing and feature extraction exactly follow the methods delineated. 62 features are used. Samples of raw and processed PPG are shown in FIG. 7.

At step 410 of the method 400, the one or more hardware processors 202 in conjunction with the user clustering and cognitive stress classification module 102 are configured to select, a subset from the plurality of feature sets, for the plurality of users associated with the primary cluster by a feature ranking method.

At step 412 of the method 400, the one or more hardware processors 202 in conjunction with the user clustering and cognitive stress classification module 102 are configured to segregate, the selected feature set of the plurality of users associated with the primary cluster into a train user dataset and a test user dataset, wherein, the test user is randomly selected from the primary cluster and the remaining users associated with the primary cluster are used as train users.

At step 414 of the method 400, the one or more hardware processors 202 in conjunction with the user clustering and cognitive stress classification module 102 are configured to train, a classifier model, using the selected feature set for the train users, for classifying the cognitive stress levels of the plurality of test users of primary cluster.

At step 416 of the method 400, the one or more hardware processors 202 in conjunction with the user clustering and cognitive stress classification module 102 are configured to classify, using the trained classifier model, the plurality of trials of the test user dataset as stressful and stressless class. Considering the above example scenario, a random forest classifier is used for training the classifier model for good performance without overfitting. Feature importances are estimated using mRMR ranking scheme on balanced data. After feature ranking, the leave one subject out cross validation (LOSOCV) method is utilized, where every training fold is balanced. F-score is chosen over accuracy as a more unbiased estimator of classification performance in presence of class imbalance. Class F (Frustration/stressful) is being considered the positive class. First, EEG features alone are ranked using the above method. Cross-validation iterations are performed on an increasing feature subset. In the ith iteration, mean of F-scores across cross-validation folds are plotted for both classes using the top i features given by mRMR. For all levels (n=10) and iterate till the top 20 features (i=1, 2 . . . 20). The performance for both high and balanced across both the classes at i=5, i.e., using only the top 5 EEG features. Features from all modalities are ranked and their performance computed in a similar manner. In this case, the best performance is seen at i=7, i.e., using the top 7 features from the whole set of EEG, PPG and GSR features. 2 out of the optimum set of 7 features are GSR features, and the top 20 contain 5 GSR features and 1 PPG feature. Some additional observations, (i) The multimodal approach decreases the disparity between F-scores of the 2 classes, compared to the EEG-only approach—performance is more balanced.
(ii) The increase in F-score, with increasing number of features, is smoother in multimodal approach and saturates at a smaller feature set—performance is more stable.
(iii) The F-score, for almost all feature sets, is higher in multimodal approach—performance improves by ~5%.

Figure 5:
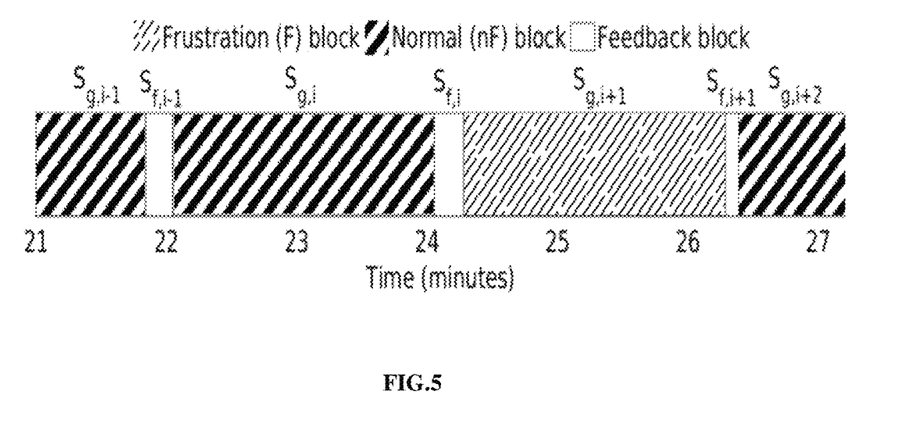
FIG. 5 illustrates example gameplays and corresponding timing sequence of physiological signals for a plurality of trials of a task performed by the user, in accordance with an embodiment of the present disclosure.

FIG. 5 illustrates example gameplays and corresponding timing sequence of physiological signals for a plurality of trials of a task performed by the user, in accordance with an embodiment of the present disclosure. In an example scenario, the gameplay trials may include difficulty levels. The AffPac or Affective Pacman dataset known technique provides data for a total of 10 levels. These datasets were created to intermittently induce stress for each user among the plurality of users. Each user played a modified version of the Pacman game, called Affective Pacman, for approximately 15 consecutive trials. Each trial lasted for 2 minutes, after which the user evaluated their experience of the trial using Self-Assessment Manikin technique. The users among the plurality of users were given option to evaluate the gameplay by choosing a rating value on a 9-point Likert scale for each of the plurality of cognitive stress parameters comprising the Valence (V) parameter, the Arousal (A) parameter and the Dominance (D) parameter. Concurrently, the next trial started immediately after user provided user evaluated feedback, resulting in f blocks of inconsistent duration. Further, the Valence (V) parameter and the Arousal (A) parameter scales were presented as inverted during feedback, such as a high numeric value (e.g. >5) on the V (or A) scale indicated low Valence (or Arousal) and vice versa and the Dominance (D) parameter scale was not inverted. To differentiate from the standard pacman gameplay, the controls consisted of pressing the left shift and right shift keys to turn the avatar 90° counter-clockwise or clockwise respectively. In a normal trial, the game progressed as expected in any popular version of Pacman. In another embodiment, while inducing stress trials, 15% of user keystrokes were ignored and there was a 5% chance of the screen freezing for 2 to 5 frames (screen refresh rate was 25 fps). Out of every 3 consecutive trials, a single trial was randomly selected to be frustrating. So, for 15 trials of a participant, 5 belong to class stressful (F), 10 belong to class stressless (nF). From every subject, physiological signals were recorded for the entire duration spanning all trials. The dataset provided EEG, GSR, PPG, EMG and EOG signals. The dataset also includes labels for F and nF trials, the plurality of user evaluated cognitive stress reports on V, A and D scales and start and end times of each trial. The dataset used provides 2 different sets of labels for each trial, wherein one set of labels consists of inferred labels, determined by the type of stimulus provided, and the other set was provided by the plurality of levels.

Figure 8:
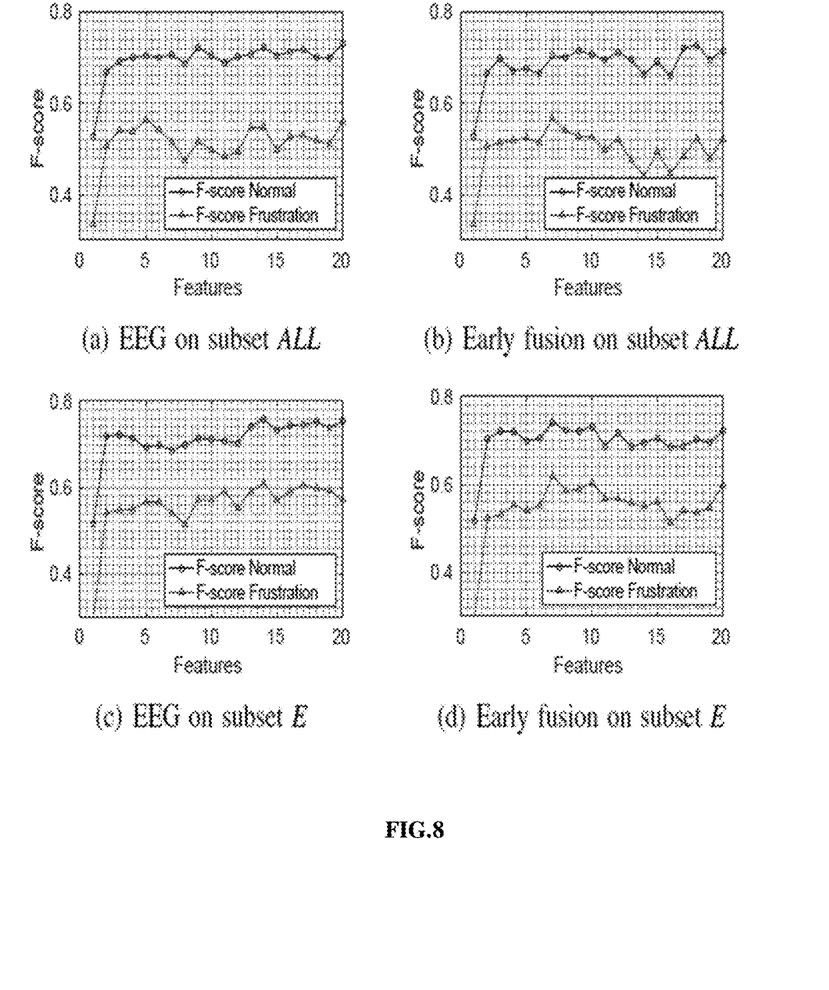
FIG. 8 illustrates performance of the proposed method depicting variation of mean F-scores of the stressful and stressless class over all leave one subject out cross validation (LOSOCV) folds utilizing the number of top features, in accordance with an embodiment of the present disclosure.

FIG. 7 illustrates observed raw and processed samples of physiological signals corresponding to EEG, GSR and PPG signals utilized in classifying cognitive stress levels of users, in accordance with an embodiment of the present disclosure, FIG. 8 illustrates performance of the proposed method depicting variation of mean F-scores of stressful class and stressless class, over all LOSOCV folds with number of top features utilized, in accordance with an embodiment of the present disclosure The proposed scheme E achieves 0.69 mean F-score. Scheme E's performance remains unaffected by early fusion. The baseline performances (performance on ALL) are F-scores of 0.61 and 0.64 respectively for EEG and early fusion. Selected feature set is optimized on subset ALL only. Improvement in performance of a subject subset can thus be attributed strongly to the fact that the subset is homogeneous with respect to cognitive response of stimuli and its reflection in the self-report. The subject subset E is formed on the basis of arousal ratings and it is found to reject high arousal levels based on the plurality of normalized cognitive stress reports.

Figure 9:
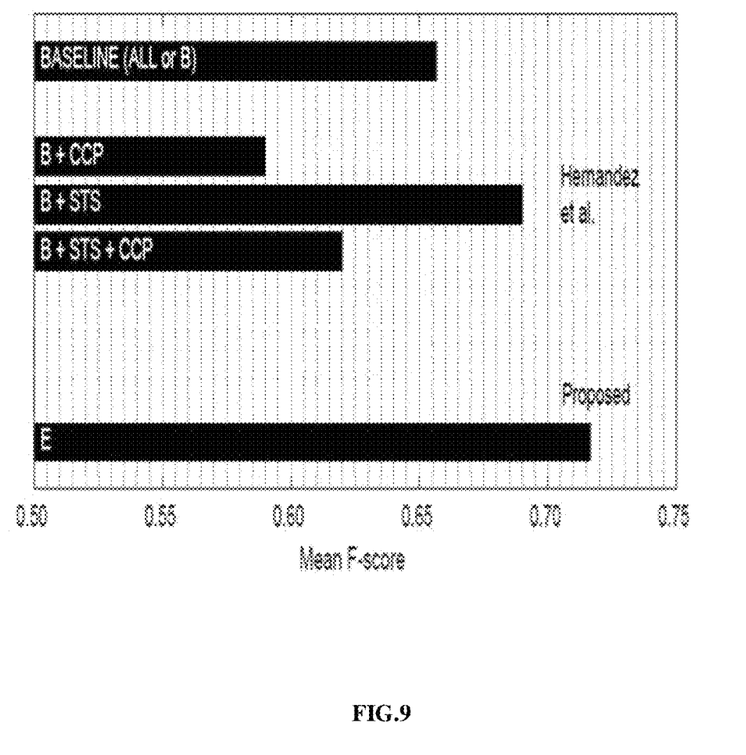
FIG. 9 illustrates performance of classifying cognitive stress levels of users in comparison with various conventional methods, in accordance with an embodiment of the present disclosure.

FIG. 9 shows the performance of classifying cognitive stress levels of users in comparison with various conventional methods, in accordance with an embodiment of the present disclosure. The system 102 replicates known techniques on the current dataset and on the features extracted by the proposed technique. The conventional methods reported performances for the following 4 methods.

B: The baseline performance, using LOSOCV, which is equivalent to our baseline ALL.
B+CCP: In the approach referred to as Changing Class Priors, they tune the misclassification cost of their SVM classifier to the prior probabilities of the test user.
B+STS: In another approach the authors tried Selecting Training Samples. The train set users were clustered by K-means (K=2) based on 2 GSR features. The classifier was trained using data only from that cluster into which the test user got classified into.
B+STS+CCP: A combination of the above approaches.

The SVM classifier was tuned in each case by trying a combination of hyperparameters that maximized a certain performance metric. The performance exhibited by ALL in the current work is shown as the baseline. As can be seen, E outperforms all the rest of the techniques. It should be noted here that in (B+STS), the features used to cluster the training set users into 2 groups might be found to correlate strongly to the features used to train the classifier. That is, features that dictate whether the test user is more similar to one group of training set users than the other, might correlate to the features from that more similar group which then train the classifier to be tested on the test user. However, the targets are different in the 2 cases. Based on the current data, it is impossible to make a comment regarding how such a choice of features might or might not affect classification performance. In the proposed work, the necessary similar group is found by clustering users based on their self-reported cognitive stress, while classification is done using features from physiological signals. A common disadvantage shared by the state-of-art and our proposed method is that they need multiple data instances from any new test user. However, both are far less data-hungry than a personalized model.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein addresses unresolved problem of user clustering and cognitive stress classification from physiological signals. The disclose system models a robust model thereby generating training data for improving classification model. The proposed method eliminates subjective bias present in cognitive stress experienced by, clustering the users and training the classifier model in a cluster-specific manner to improve efficiency of stress detection from the physiological signals. The embodiment, thus provides homogeneous groups on the basis of self-reported cognitive stress for similar stimuli, and draw training and test levels from the same group to build a model to classify the nature of those stimuli. In addition, the system extends incorporating to form independent rudimentary cohorts for any physiological signals depending on self-reported cognitive stress reports. Moreover, the disclosed system validates cognitive stress levels for larger number of public datasets. Larger datasets shall, in turn, reveal which dimensions, among Valence, Arousal and Dominance, are more significant in grouping levels as similar and how much the choice of dimension depends on the problem being targeted. It would also be interesting to conduct a similar longitudinal study focusing on the effect of medication, for stress, anxiety or depression, on the self-assessments of levels and the cohorts to which they are assigned.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor implemented method for clustering users for classifying cognitive stress levels, the method comprising:
receiving
a plurality of cognitive stress reports recorded for a plurality of users while performing a task comprising a plurality of levels, wherein each cognitive stress report among the plurality of cognitive stress reports corresponds to a user among the plurality of users, and each cognitive stress report records user-evaluated estimate of the cognitive stress experienced by each user at each level among the plurality of levels repeated for a plurality of trials performed for the task by the user,
wherein, each cognitive stress report comprises a plurality of cognitive stress parameters recorded for the plurality of levels during the performance of the task, and
a plurality of physiological signals for each user from a plurality of sensors;
generating a plurality of normalized cognitive stress report for each user, wherein the normalized cognitive stress comprises an estimate of the cognitive stress experienced by the user at each level of the task for the plurality of trials;
clustering the plurality of users based on the plurality of normalized cognitive stress reports using an unsupervised clustering mechanism to generate a primary cluster and a secondary cluster, such that users of each cluster have similar distribution of normalized cognitive stress reports for the plurality of trials of the task and users of different clusters have dissimilar distribution of normalized cognitive stress reports for the plurality of trials of the task;
extracting a plurality of feature sets from the plurality of physiological signals, the plurality of feature sets correlating with the cognitive stress experienced by the plurality of users associated with the primary cluster;
selecting, using a feature ranking method, a subset from the plurality of feature sets for the plurality of users associated with the primary cluster;
segregating the selected feature set of the plurality of users associated with the primary cluster into a train user dataset and a test user dataset, wherein, the test user is randomly selected from the primary cluster and the remaining users associated with the primary cluster are used as train users;
training, using the selected feature set of the train user dataset, a classifier model for classifying stressful and stressless trials for the users of primary cluster; and
classifying, using the trained classifier model, the plurality of trials of the test user dataset as stressful and stressless class.

2. The method as claimed in claim 1, wherein the plurality of physiological signals comprise Electroencephalogram (EEG) signal to estimate the neural responses of the user, Photoplethysmogram (PPG) signal to analyze cardiac parameters of the user, and Galvanic Skin Response (GSR) to determine changes due to variations in skin conductance of the user.

3. The method as claimed in claim 1, wherein the plurality of cognitive stress parameters comprise a valence parameter, an arousal parameter and a dominance parameter.

4. The method as claimed in claim 1, wherein, the plurality of normalized cognitive stress reports are generated for each user for the plurality of cognitive stress parameters using a mode value and a range value.

5. The method as claimed in claim 4, wherein the mode value for generating the normalized cognitive stress report for the plurality of cognitive stress parameters is determined by
identifying frequently reported estimate of cognitive stress of each user for each cognitive stress parameter for the plurality of trials experienced while performing the task, wherein the cognitive stress report of each user of all trials, the mode of subscript estimate of user evaluated cognitive stress at each level, to the superscript of each parameter associated with the plurality of cognitive stress parameters.

6. The method as claimed in claim 4, wherein the range value for generating the normalized cognitive stress report for the plurality of cognitive stress parameters is determined by
obtaining the difference between the highest value and the lowest value of the user evaluated cognitive stress from the plurality of cognitive stress reports for all trials of the plurality of cognitive stress parameter experienced while performing the task.

7. The method as claimed in claim 1, wherein the normalized cognitive stress report for the plurality of cognitive stress parameters is generated using the mode value and the range value by
subtracting the mode of the cognitive stress parameter for the user evaluated estimate of the cognitive stress parameter for the plurality of trials and dividing the resulting mode value by one-fifth of the range of the plurality of cognitive stress parameters for each user among the plurality of users.

8. A system for classification of cognitive stress of users, wherein the system comprises:
a processor;
an input/output (I/O) interface; and
a memory coupled to the processor, the memory storing instructions executable by the processor to:
receive
a plurality of cognitive stress reports recorded for a plurality of users while performing a task comprising a plurality of levels, wherein each cognitive stress report among the plurality of cognitive stress reports corresponds to a user among the plurality of users, and each cognitive stress report records user-evaluated estimate of the cognitive stress experienced by each user at each level among the plurality of levels repeated for a plurality of trials performed for the task by the user,
wherein, each cognitive stress report comprises a plurality of cognitive stress parameters recorded for the plurality of levels during the performance of the task, and
a plurality of physiological signals for each user from a plurality of sensors;
generate a plurality of normalized cognitive stress report for each user, wherein the normalized cognitive stress comprises an estimate of the cognitive stress experienced by the user at each level of the task for the plurality of trials;
cluster the plurality of users based on the plurality of normalized cognitive stress reports using an unsupervised clustering mechanism to generate a primary cluster and a secondary cluster such that users of each cluster have similar distribution of normalized cognitive stress reports for the plurality of trials of the task and users of different clusters have dissimilar distribution of normalized cognitive stress reports for the plurality of trials of the task;

extract a plurality of feature sets from the plurality of physiological signals, the plurality of feature sets correlating with the cognitive stress experienced by the plurality of users associated with the primary cluster;

select a subset from the plurality of feature sets for the plurality of users associated with the primary cluster by a feature ranking method;

segregate the selected feature set of the plurality of users associated with the primary cluster into a train user dataset and a test user dataset, wherein, the test user is randomly selected from the primary cluster and the remaining users associated with the primary cluster are used as train users;

train, using the selected feature set for the train users, a classifier model for classifying stressful and stressless trials for the users of primary cluster; and classify, using the trained classifier model, the plurality of trials of test user as stressful and stressless class.

9. The system as claimed in claim 8, wherein the plurality of physiological signals comprises Electroencephalogram (EEG) signal to estimate the neural responses of the user, Photoplethysmogram (PPG) signal to analyze cardiac parameters of the user, and Galvanic Skin Response (GSR) to determine changes due to variations in skin conductance of the user.

10. The system as claimed in claim 8, wherein the plurality of cognitive stress parameters comprises a valence parameter, an arousal parameter and a dominance parameter.

11. The system as claimed in claim 8, wherein, the plurality of normalized cognitive stress reports are generated for each user for the plurality of cognitive stress parameters using a mode value and a range value.

12. The system as claimed in claim 11, wherein the mode value for generating the normalized cognitive stress report for the plurality of cognitive stress parameters is determined by identifying frequently reported estimate of cognitive stress of each user for each cognitive stress parameter for the plurality of trials experienced while performing the task, wherein the cognitive stress report of each user of all trials, the mode of subscript estimate of user evaluated cognitive stress at each level to the superscript of each parameter associated with the plurality of cognitive stress parameters.

13. The system as claimed in claim 11, wherein the range value for generating the normalized cognitive stress report for the plurality of cognitive stress parameters is determined by, obtaining the difference between the highest value and the lowest value of the user evaluated cognitive stress from the plurality of cognitive stress reports for all trials of the plurality of cognitive stress parameter experienced while performing the task.

14. The system as claimed in claim 8, wherein the normalized cognitive stress report for the plurality of cognitive stress parameters is generated using the mode value and the range value by, subtracting the mode of the cognitive stress parameter for the user evaluated estimate of the cognitive stress parameter for the plurality of trials and dividing the resulting mode value by one-fifth of the range of the plurality of cognitive stress parameters for each user among the plurality of users.

15. One or more non-transitory machine readable information storage media storing instructions which, when executed by one or more hardware processors, cause the one or more hardware processors to perform actions comprising:

receiving a plurality of cognitive stress reports recorded for a plurality of users while performing a task comprising a plurality of levels, wherein each cognitive stress report among the plurality of cognitive stress reports corresponds to a user among the plurality of users, and each cognitive stress report records user-evaluated estimate of the cognitive stress experienced by each user at each level among the plurality of levels repeated for a plurality of trials performed for the task by the user, wherein, each cognitive stress report comprises a plurality of cognitive stress parameters recorded for the plurality of levels during the performance of the task, and a plurality of physiological signals for each user from a plurality of sensors;

generating a plurality of normalized cognitive stress report for each user, wherein the normalized cognitive stress comprises an estimate of the cognitive stress experienced by the user at each level of the task for the plurality of trials;

clustering the plurality of users based on the plurality of normalized cognitive stress reports using an unsupervised clustering mechanism to generate a primary cluster and a secondary cluster, such that users of each cluster have similar distribution of normalized cognitive stress reports for the plurality of trials of the task and users of different clusters have dissimilar distribution of normalized cognitive stress reports for the plurality of trials of the task;

extracting a plurality of feature sets from the plurality of physiological signals, the plurality of feature sets correlating with the cognitive stress experienced by the plurality of users associated with the primary cluster;

selecting, using a feature ranking method, a subset from the plurality of feature sets for the plurality of users associated with the primary cluster;

segregating the selected feature set of the plurality of users associated with the primary cluster into a train user dataset and a test user dataset, wherein, the test user is randomly selected from the primary cluster and the remaining users associated with the primary cluster are used as train users;

training, using the selected feature set of the train user dataset, a classifier model for classifying stressful and stressless trials for the users of primary cluster; and classifying, using the trained classifier model, the plurality of trials of the test user dataset as stressful and stressless class.

16. The one or more non-transitory machine readable information storage media of claim 15, wherein the plurality of physiological signals comprise Electroencephalogram (EEG) signal to estimate the neural responses of the user, Photoplethysmogram (PPG) signal to analyze cardiac parameters of the user, and Galvanic Skin Response (GSR) to determine changes due to variations in skin conductance of the user.

17. The one or more non-transitory machine readable information storage media of claim 15, wherein the plurality of cognitive stress parameters comprise a valence parameter, an arousal parameter and a dominance parameter.

18. The one or more non-transitory machine readable information storage media of claim 15, wherein the plurality of normalized cognitive stress reports are generated for each user for the plurality of cognitive stress parameters using a mode value and a range value.

19. The one or more non-transitory machine readable information storage media of claim 18, wherein the mode value for generating the normalized cognitive stress report for the plurality of cognitive stress parameters is determined by identifying frequently reported estimate of cognitive stress of each user for each cognitive stress parameter for the plurality of trials experienced while performing the task, wherein the cognitive stress report of each user of all trials, the mode of subscript estimate of user evaluated cognitive stress at each level, to the superscript of each parameter associated with the plurality of cognitive stress parameters.

20. The one or more non-transitory machine readable information storage media of claim 18, wherein the range value for generating the normalized cognitive stress report for the plurality of cognitive stress parameters is determined by obtaining the difference between the highest value and the lowest value of the user evaluated cognitive stress from the plurality of cognitive stress reports for all trials of the plurality of cognitive stress parameter experienced while performing the task.

* * * * *